United States Patent [19]

Konishi et al.

[11] Patent Number: 5,546,158
[45] Date of Patent: Aug. 13, 1996

[54] VIEW POINT DETECTING APPARATUS WHEREIN FIRST AND SUBSEQUENT VIEW POINT DATA ARE COMPARED

[75] Inventors: Kazuki Konishi, Tokyo; Akihiko Nagano, Ichihara, both of Japan

[73] Assignee: Canon Kabushiki Kaisha, Tokyo, Japan

[21] Appl. No.: 445,718

[22] Filed: May 22, 1995

Related U.S. Application Data

[63] Continuation of Ser. No. 161,523, Dec. 6, 1993, abandoned, which is a continuation of Ser. No. 881,775, May 12, 1992, abandoned.

[30] Foreign Application Priority Data

May 13, 1991 [JP] Japan ............ 3-107311
May 13, 1991 [JP] Japan ............ 3-107316
May 13, 1991 [JP] Japan ............ 3-107317

[51] Int. Cl.$^6$ .................................... G03B 7/00
[52] U.S. Cl. .......................... 354/410; 354/62
[58] Field of Search ...................... 354/400, 402, 354/410, 62; 351/210

[56] References Cited

U.S. PATENT DOCUMENTS

| | | | |
|---|---|---|---|
| 4,574,314 | 3/1986 | Weinblatt | 354/400 |
| 4,836,670 | 6/1989 | Hutchinson | 354/62 |
| 4,950,069 | 8/1990 | Hutchinson | 354/62 |
| 4,973,149 | 11/1990 | Hutchinson | 351/210 |
| 4,974,010 | 11/1990 | Cleveland et al. | 354/62 |
| 5,036,347 | 7/1991 | Tsunekawa et al. | 354/400 |
| 5,138,359 | 8/1992 | Nagano et al. | 354/406 |
| 5,214,466 | 5/1993 | Nagano et al. | 354/402 |
| 5,225,862 | 7/1993 | Nagano et al. | 354/62 |
| 5,253,008 | 10/1993 | Konishi et al. | 354/402 |
| 5,262,807 | 11/1993 | Shindo | 351/210 |
| 5,333,029 | 7/1994 | Uchiyama et al. | 354/410 |

FOREIGN PATENT DOCUMENTS

| | | |
|---|---|---|
| 0237554 | 9/1987 | European Pat. Off. . |
| 4034958 | 5/1991 | Germany . |
| 63-94232 | 4/1988 | Japan . |
| 3-219218 | 9/1991 | Japan . |
| WO8701571 | 3/1987 | WIPO . |

OTHER PUBLICATIONS

Mitsuho Yamada and Tadahiko Fukuda, "Analysis of Television Picture Using Eye Movement", *Television Society Journal*, vol. 40, No. 2 (1986), pp. 41–48 (Japanese publication and partial translation thereof).

*Primary Examiner*—Russell E. Adams
*Attorney, Agent, or Firm*—Fitzpatrick, Cella, Harper & Scinto

[57] ABSTRACT

View point detecting apparatus wherein first and subsequent view point data are compared includes state detecting structure for detecting the state of an observer's view point. Circuitry is provided for determining, when amounts of a variation between a first view point information and a subsequent view point information exceed a predetermined value, that the first view point information is effective. Preferably, structure is also provided for adjusting a phototaking lens on the basis of the first view point information.

23 Claims, 15 Drawing Sheets

$$\ast \Delta 1 = \sqrt{(x_i - x_{i-1})^2 + (y_i - y_{i-1})^2}$$

$$ \ast \Delta 1 = \sqrt{(x_i - x_{i-1})^2 + (y_i - y_{i-1})^2} $$

$$※ \Delta 1 = \sqrt{(x_i - x_{i-1})^2 + (y_i - y_{i-1})^2}$$

$$ \ast \Delta 1 = \sqrt{(x_i - x_{i-1})^2 + (y_i - y_{i-1})^2} $$

VIEW POINT DETECTING APPARATUS WHEREIN FIRST AND SUBSEQUENT VIEW POINT DATA ARE COMPARED

This application is a continuation of application Ser. No. 08/161,523 filed Dec. 6, 1993, which is a continuation of Ser. No. 07/881,775, filed May 12, 1992, both now abandoned.

BACKGROUND OF THE INVENTION

1. Field of the Invention

This invention relates to a view point detecting apparatus suitable for use in a video camera, a still camera or the like.

2. Related Background Art

Various ideas of using the photographer's visual axis (so-called automatic pursuit using the visual axis) to determine an area for controlling the operations of a camera have heretofore been proposed, and for example, in Japanese Laid-Open Patent Application No. 63-94232, a description has been provided as follows.

FIG. 8 of the accompanying drawings shows a block diagram of a construction according to the prior art.

In this example of the prior art, the movement of the eyeball of the photographer observing a photographed image through a finder or a monitor device is monitored and the automatic focusing operation and the automatic exposure operation are performed in an area including that portion of the image field which is gazed at by the photographer. The reference numeral 30 designates a detector of eye movement. This detector 30, the details of which will be described later, detects the movement of the photographer's eyeball 32, and sends to a gate control circuit 34 a position signal (horizontal position and vertical position) indicative of which position in the image field the eye is looking at. The gate control circuit 34 compares a horizontal synchronizing signal Hsync and a vertical synchronizing signal Vsyn from a clock circuit 28 with the position signal from the detector of eye movement 30, controls a gate circuit 14 and passes therethrough only the image signal of a corresponding area on the image field.

There are various principles of detecting eye movement, and herein the system of Nippon Hōsō Kyokai (NHK) will be described as an example (see Television Society journal vol. No. 2 (1986), p. 41 and so on). The optical system portion of the NHK's system is shown in FIG. 9 of the accompanying drawings, and a specific circuit when it is applied to the detector of eye movement 30 in the embodiment of FIG. 8 is shown in FIG. 10 of the accompanying drawings with the gate control circuit 34. As shown in FIG. 9, infrared light is applied from an infrared light source 40 (40X, 40Y) disposed in proximity to the eyeball, and the reflected light therefrom is received by photoelectric conversion elements 42 (42R, 42L; 42U, 42D) and the rightward and leftward movement and upward and downward movement of the iris are detected. The photoelectric conversion elements 42R and 42L for detecting the rightward and leftward movement of the iris are disposed so as to receive the reflected lights from the right side and the left side, respectively, of the iris in a front-facing state, and the outputs thereof are subtraction-amplified by a subtract amplifier 44. Also, the photoelectric conversion elements 42U and 42D for detecting the upward and downward movement of the iris are both disposed so as to receive the reflected light from the obliquely lower position of the iris in a front-facing state, and the outputs thereof are addition-amplified by an add amplifier 46.

The output of the subtract amplifier 44 exhibits the characteristic as shown in FIG. 11A of the accompanying drawings to the rightward and leftward movement of the iris, and the output of the add amplifier 46 exhibits the characteristic as shown in FIG. 11B of the accompanying drawings to the upward and downward movement of the iris. After all, the output of the subtract amplifier 44 indicates the direction of the iris in the horizontal plane (speaking in terms of the observation image field being observed by the observer, the horizontal position thereof), and the output of the add amplifier 46 indicates the direction in which the iris faces in the vertical plane (speaking in terms of the observation image field, the vertical position thereof). Actually, however, the outputs of the subtract amplifier 44 and the add amplifier 46 exhibit more or less non-linearity and therefore, it is preferable to provide linearity compensation circuits 48 and 50 in order to enhance detection accuracy.

Accordingly, in FIG. 10, the output of a compensation circuit 48 indicates a horizontal position x in the image field image and the output of a compensation circuit 50 indicates a vertical position y in the image field image.

Also, the assignee has proposed apparatuses for detecting the visual axis in U.S. Pat. No. 5,036,347, U.S. applications Ser. Nos. 406,588 (filed on Sep. 13, 1989), and 746,462 (filed on Aug. 16 1991), U.S. Continuation applications Nos. 671,656 (filed on Mar. 19, 1991) and 807,621 (filed on Dec. 13, 1991).

However, in the above-described examples of the prior art, even if the photographer's visual axis can be detected, the visual axis is detected as having likewise shifted when the photographer momentarily looks, for example, at the outside of the frame of the required photographing image field and the change-over or the like of the AF area based on the visual axis is effected and therefor, the reverse effect of using visual axis detection is provided.

SUMMARY OF THE INVENTION

The present invention has as its first object the provision of an apparatus in which, paying attention to eyeball movement based on physiology, for example, saccadic movement or the minute movement in a gazing state, detects the view point more accurately.

Also, the present invention has as its second object the provision of an apparatus in which, when under the first object, the view point is to be changed by a detecting apparatus, permits the change when a predetermined condition is satisfied.

DETAILED DESCRIPTION OF THE PREFERRED EMBODIMENTS

Figure 1:
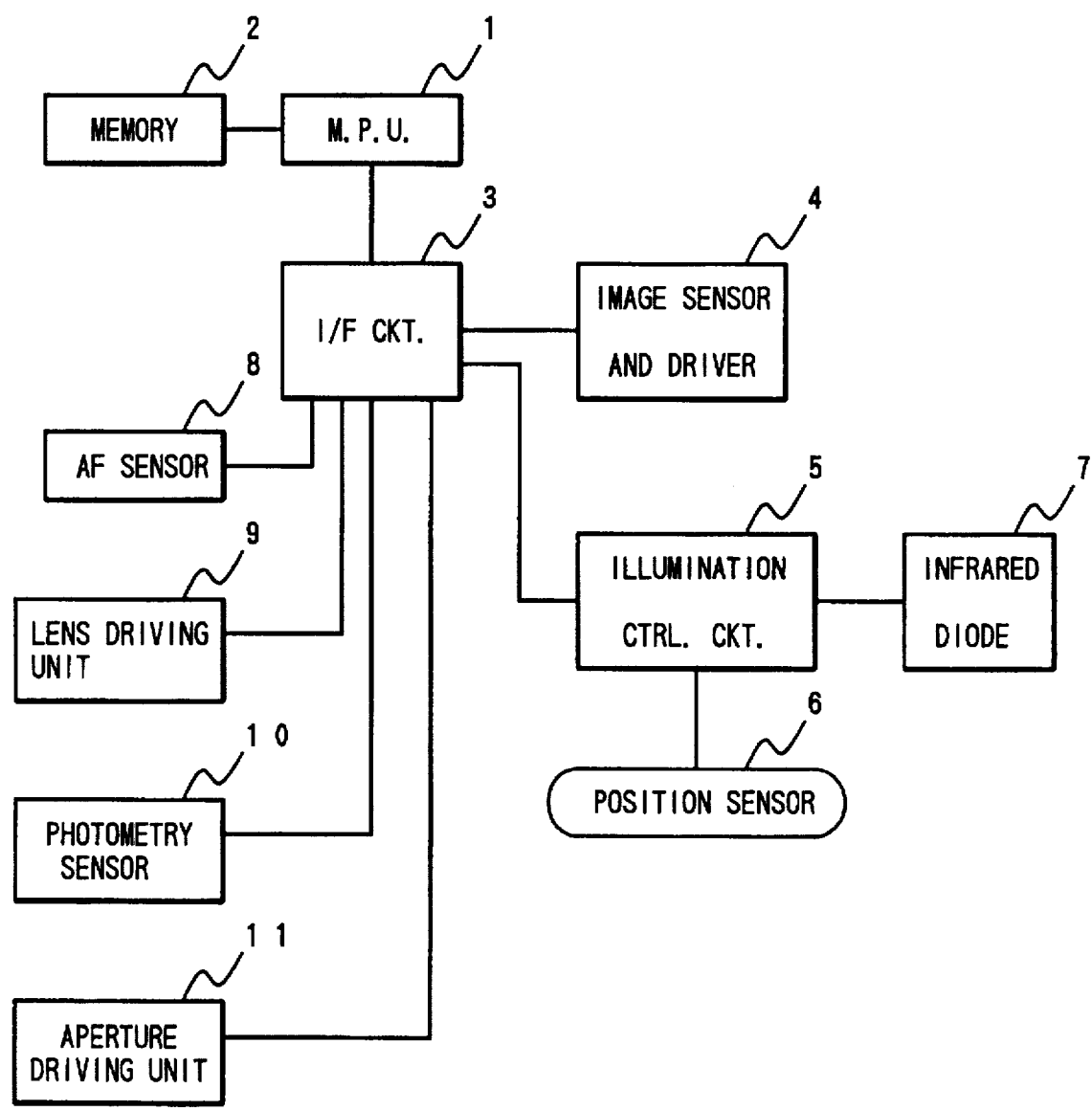
FIG. 1 is a block diagram of a first embodiment of the present invention.

Referring to FIG. 1 which is a block diagram of a first embodiment of the present invention, the reference numeral 1 designates an M.P.U. (micro-processing unit), the reference numeral 2 denotes a memory, the reference numeral 3 designates an interface circuit having the A/D converting function, the reference numeral 4 denotes a sensor unit comprising an image sensor for observing the photographer's eyeball and a driving circuit therefor, and the reference numeral 7 designates an infrared diode as a light emitting diode for illuminating the observer's eye. The reference numeral 5 denotes an illumination control circuit, the reference numeral 6 designates a position sensor for detecting the vertical position and horizontal position of a camera, the reference numeral 8 denotes an AF sensor for detecting the focus state of a photo-taking lens, the reference numeral 9 designates a lens driving unit, the reference numeral 10 denotes a photometry sensor, and the reference numeral 11 designates an aperture driving unit.

In the present embodiment, an image signal from an image sensor is calculated to thereby find the photographer's visual axis, and the principle thereof is as follows. When parallel light (or divergent light) is applied to the photographer's eyeball by the light emitting diode 7, this light is reflected by the front face of the cornea and there is created a virtual image of the light emitting diode. This virtual image is called a Purkinje image, and the position at which this image is created coincides with the center of the pupil when the rotation angle of the eyeball is zero, and as the eyeball rotates, the spacing between the Purkinje image and the center of the pupil widens substantially in proportion to the sine of the rotation angle. Consequently, the position of the Purkinje image, the position of the center of the pupil and further the spacing therebetween are calculated from the image signal on the image sensor, the rotation angle of the eyeball and further the photographer's view point can be known (by the optical characteristic of the finder of the camera, even if the head moves relative to the camera, the view point on a focusing screen remains unchanged if the rotation angle of the eyeball is equal).

The operation of the present embodiment using the above-described principle will now be described with reference to the flow chart of FIG. 2.

When the main switch (not shown) of the camera is closed and the starting of visual axis detection is instructed, the M.P.U. 1 shifts control to the visual axis detection routine (step 10).

When the visual axis detection routine is entered, the initializing process is first carried out and the values of all variables concerned with visual axis detection are rendered into zero (step 11). The information of the then position (the vertical position or the horizontal position) of the camera is received from the position sensor 6, and the illumination control circuit 5 effects the setting of which of the groups of infrared diodes (iRED) should be made to emit light. At the same time, the M.P.U. 1 gives an integrated signal to the image sensor driving circuit 4 and an illumination control signal synchronized with the integrated signal to the illumination control circuit 5, through the interface circuit 3. Thereby, the infrared diode which corresponds to the then position of the camera is made to emit light in synchronism with the accumulation by the image sensor (step 12). Then, the image of the front eye portion of the eye in which the Purkinje image formed on the image sensor 4 is created is read through the interface circuit 3 (step 13). By this image being processed, the positions $D_1$, $D_2$ and $D_3$ of at least three pupil edges are detected as the position P of the Purkinje image (step 14). From the thus detected amounts, the rotation angles $\theta_H$ and $\theta_V$ of the eyeball in the horizontal direction and the vertical direction are calculated. When the rotation angles of the eyeball are calculated, individual difference correction such as visual axis correction is effected to thereby find the photographer's view point on the focusing screen, and the view point is found from the stay time thereof or the like (step 15). Further, from this view point, an area for effecting focus detection when AF is instructed, i.e., the so-called AF area, and the AE area for effecting exposure control are determined (step 16).

Now, generally in a camera using silver salt film, if AF points are increased, the same number of distance measuring units as the AF points will be required. Therefore, from the demerits in cost and space, the number of AF points is limited. Accordingly, there is the possibility that the AF point corresponding to the view point position on the focusing screen does not exist. So, compensation is effected in the following manner.

Figure 3A:
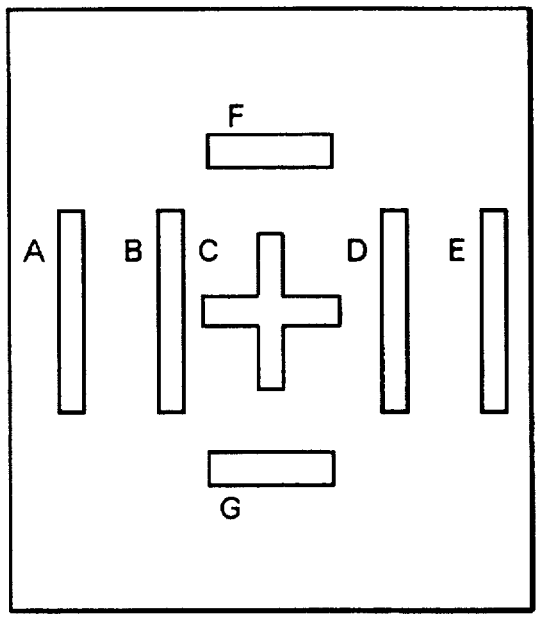
FIGS. 3A and 3B show AF and AE areas.

A first method is that where the AF area corresponding to the view point on the focusing screen does not exist, the AF point nearest from the view point on the focusing screen is defined as the AF point of that view point. For example, where the AF point is set as shown in FIG. 3A, the coordinates (x, y) of the view point position are found as the distance 1 of the central coordinates $(x_A, y_A)$ $(x_B, y_B)$ $(x_C, y_C)$ $(x_D, y_D)$ $(x_E, y_E)$ $(x_F, y_F)$ $(x_G, y_G)$ of seven AF points A–G from the following equation and that point at which the value of said distance is minimum is defined as the AF point of that view point position.

$$1 = \sqrt{(x-x_a)^2 + (y-y_a)^2}$$

(the case of AF point A)

Figure 3B:
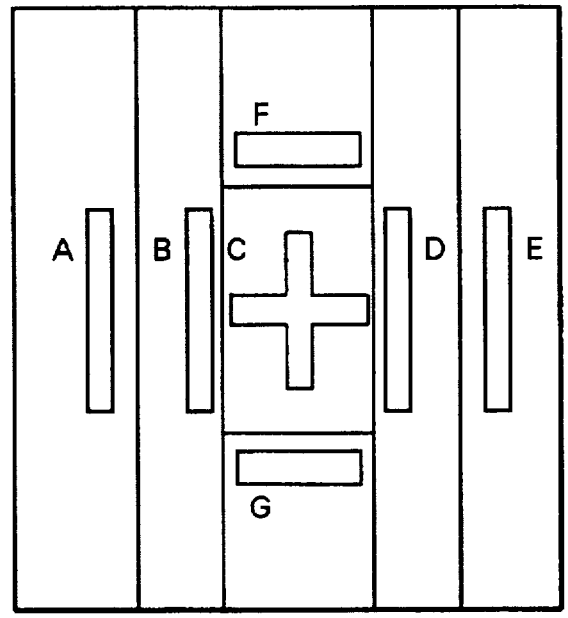

A second method is that an AF point and an area which selects that AF point are preset. For example, the AF points A–G and areas which select them are set as shown in FIG. 3B.

This also holds true of the determination of the AE area, but the photometry sensor used is often one having its area divided and therefore, the second method becomes the main method. That is, provision is made of a photometry device which divisionally meters so as to correspond to the seven large areas of FIG. 3B.

Figure 4:
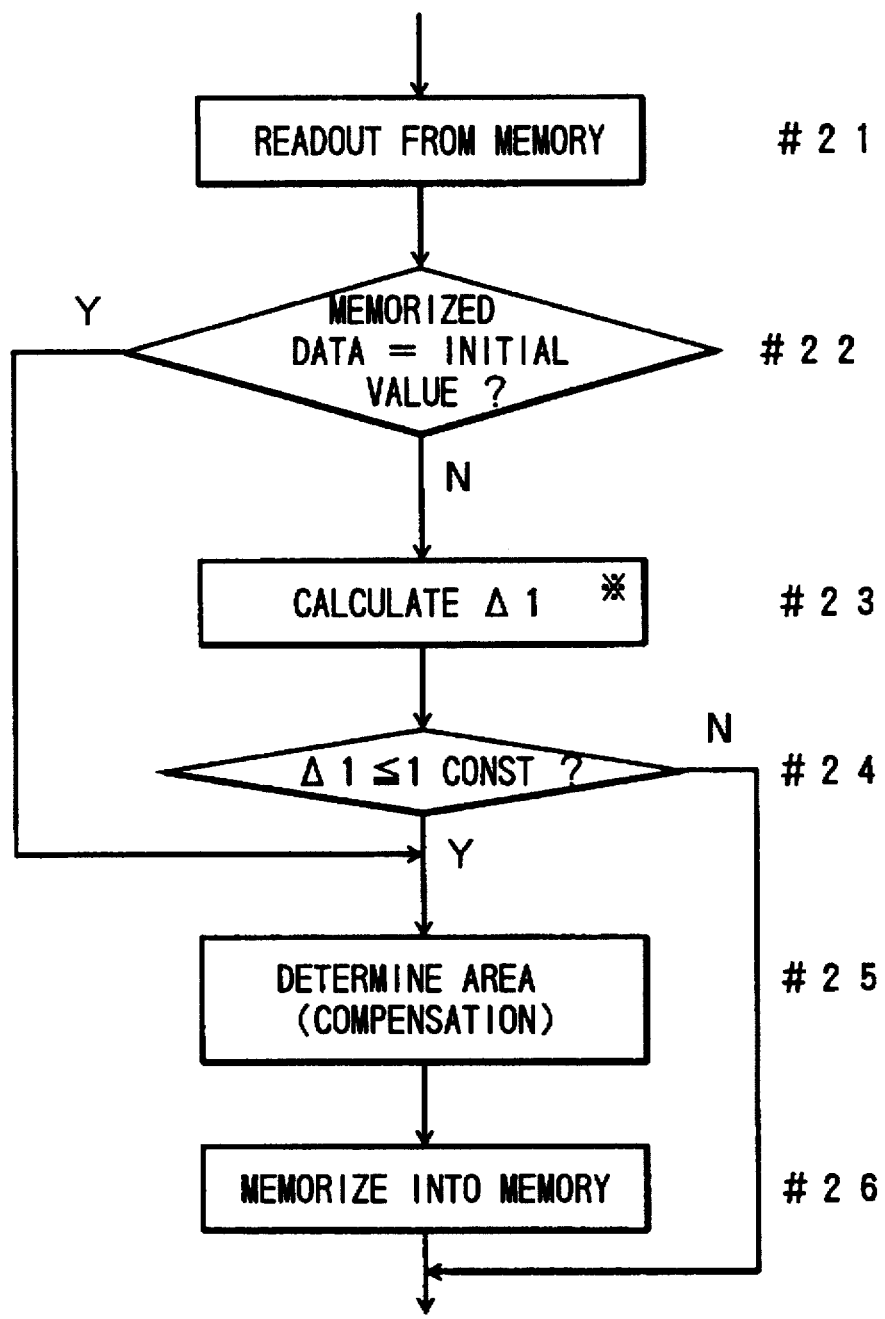
FIG. 4 is a flow chart of an operation for effecting the area determination of the first embodiment.

Now, the actual photographer's view point is not always on an object to be photographed, but feels dizzy to some degree or locks at the display outside the image field. So, when the view point lies outside the image field, it becomes necessary to bring the view point out of the object of the pursuing operation or to extract the photographer's view point by a conventional technique. Further, in the present embodiment, in order to perform the pursuing operation effectively, the movement of the AF–AE (auto-exposure) area is not effected when the amount of movement of the view point exceeds a predetermined value. The procedure of that operation is shown in FIG. 4. When the AF-AE area determination routine is entered from the gaze position, the information of the AF and AE areas at the last gaze position memorized in the memory is first read (step 21). If it is an initialized value, that is, if this is the first area determining operation (step 22), the compensation as described above is effected on the basis of the then position of the view point to thereby determine the area (step 25), and the information thereof is memorized into the memory (step 26). In the case of the second or subsequent area determining operation, comparison with the information of the last AF and AE area and whether there has been great movement is judged. If the x coordinates and y coordinates of the view point position used during the determination of the AF and AE area are memorized as the information of the AF and AE area, the distance $$\Delta 1 \ (= \sqrt{(x_i - x_{i-1})^2 + (y_i - y_{i-1})^2})$$

between the view point position coordinates $(x_i, y_i)$ found this time and the last view point position coordinates $(x_{i-1}, y_{i-1})$ is found (step 23), and if this value is equal to or less than a predetermined value 1const (step 24), the above-described compensation is further effected by the use of the coordinates of the view point found this time to thereby determine the area of a new gaze position, and the information thereof is memorized into the memory. If conversely, $\Delta 1$ exceeds 1const, the area information found the last time is not renewed but is intactly used.

The purpose of carrying out such a process is to minimize a detection error attributable to the characteristic of man's eyeball movement and suppress an inconvenience such as cumbersome lens movement caused by changing over the AF and AE areas.

The characteristic of the eyeball movement taken up here as a subject is saccadic movement. Saccadic movement is eyeball movement occurring during reading or when one gazes at the feature of an image, and its movement time is 1/20 to 1/100 second and its maximum speed amounts to 300 degrees/sec. But the period of its occurrence is a short interval of 0.2 second or less, and further, in the movement state from 50 msec. before the occurrence of the movement till the termination of the movement, there is seen the phenomenon that a visual function called saccadic suppression is extremely reduced.

Accordingly, with regard to an erroneous operation caused by detecting a point in the course of movement to the movement termination point when saccadic movement has occurred, particularly to saccadic movement which has occurred to see the display outside the finder view field, it is expected that a great inconvenience will occur if the point in the course of movement is detected. Consequently, the constant 1const is determined by pursuing movement (which is slow and smooth eyeball movement occurring when one pursues a moving object slowly, and occurs for a moving object of 30–35 degrees/sec. or less) and visual axis detection interval. Thus, the constant 1const is determined in the form of the product of the amount of movement 1smooth of the view point on the focusing screen of the camera caused by the pursuing movement and the visual axis detection interval Tsample.

When a photometry switch SW1 is closed (step 17), the AF operation and photometry are effected (steps 18 and 19). In the AF operation, the M.P.U. first reads a defocus signal from the AF sensor in the area corresponding to the gaze position, and calculates a signal to thereby find the amount of lens driving. Thereafter, the M.P.U. controls the lens driving unit and effects focus adjustment. Also, the M.P.U. weights the area corresponding to the gaze position and finds the photometry value on the basis of the signals from the divisional photometry sensors for all areas, and determines exposure constants (shutter speed, aperture value, etc.) in accordance with a designated photographing mode.

When the second-stage operation of the release button is performed and the requirements for release are finished (step 20), a series of operations regarding release, such as the driving of the aperture to the calculated aperture value, the mirror operation, the opening and closing of the shutter and the winding of film are performed.

In the description hitherto made, the AF operations (signal reading→calculation→lens driving) and photometry have been described as being performed substantially at a time, but in the actual camera, these conform to a mode set in the camera. That is, in the mode setting of the camera, photometry may be effected immediately before release and the exposure value may be determined on the basis of the photometric value.

Also, of the AF operations, only lens driving may be effected after release has been demanded.

As has hitherto been described, the present embodiment is one which carries out so-called automatic object pursuit in which the movement of the photographer's visual axis is detected and AF and AE are effected in an area wherein the visual axis exists.

Figure 5:
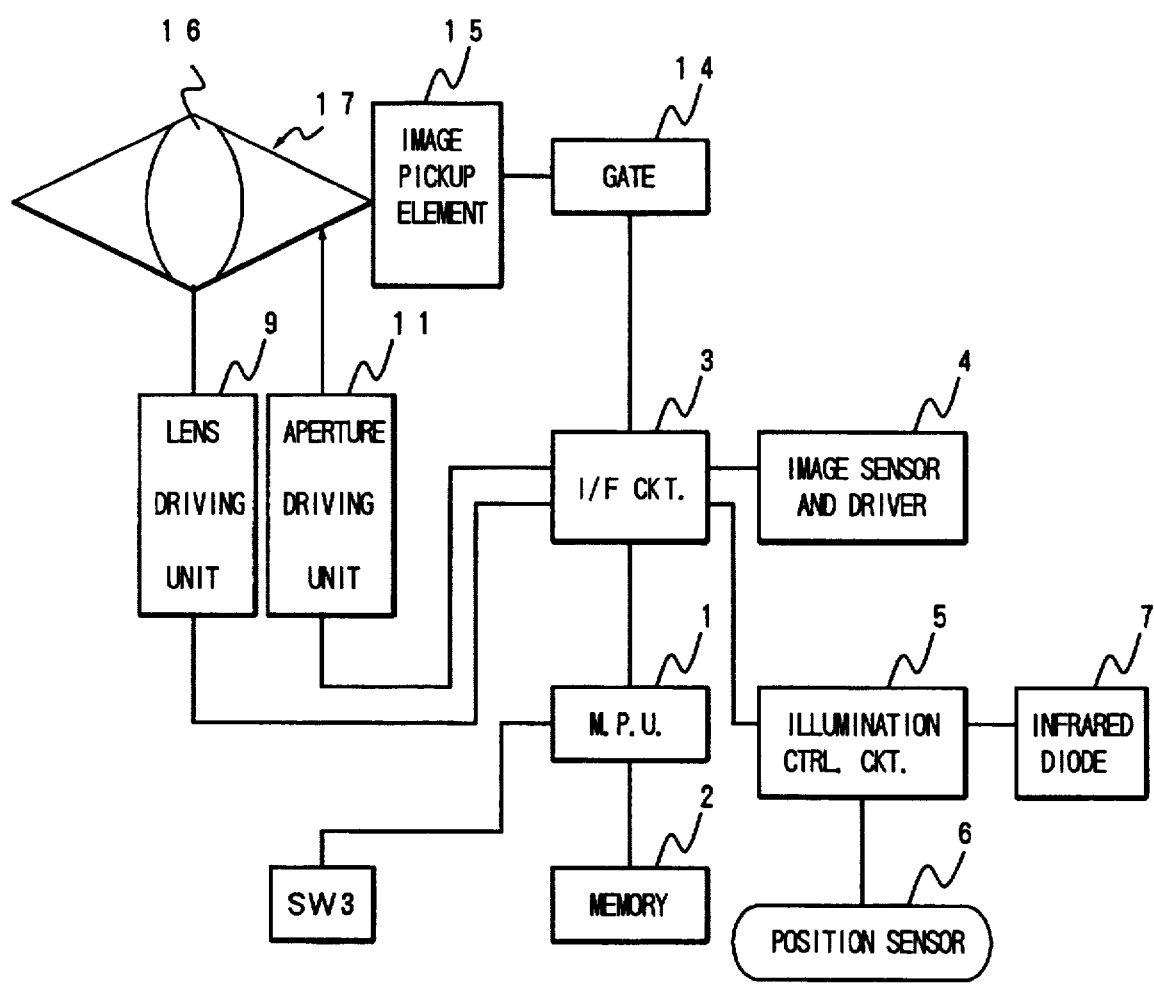
FIG. 5 is a block diagram of a second embodiment of the present invention.

FIG. 5 shows a block diagram of a second embodiment.

The reference numeral 1 designates an M.P.U., the reference numeral 2 denotes a memory, the reference numeral 3 designates an interface circuit, the reference numeral 7 denotes an infrared diode, the reference numeral 9 designates a lens driving unit, the reference numeral 11 denotes an aperture driving unit, the reference numeral 15 designates an image pickup element for photographing, the reference numeral 16 denotes a photo-taking lens, the reference numeral 17 designates an aperture unit, and the reference numeral 14 denotes a gate.

The first embodiment is a system suitable for a silver salt still camera, whereas the second embodiment is a system suitable for a video camcorder or the like. Also, the principle of visual axis detection, like that of the first embodiment, uses a Purkinje image and the center of the pupil.

Figure 6:
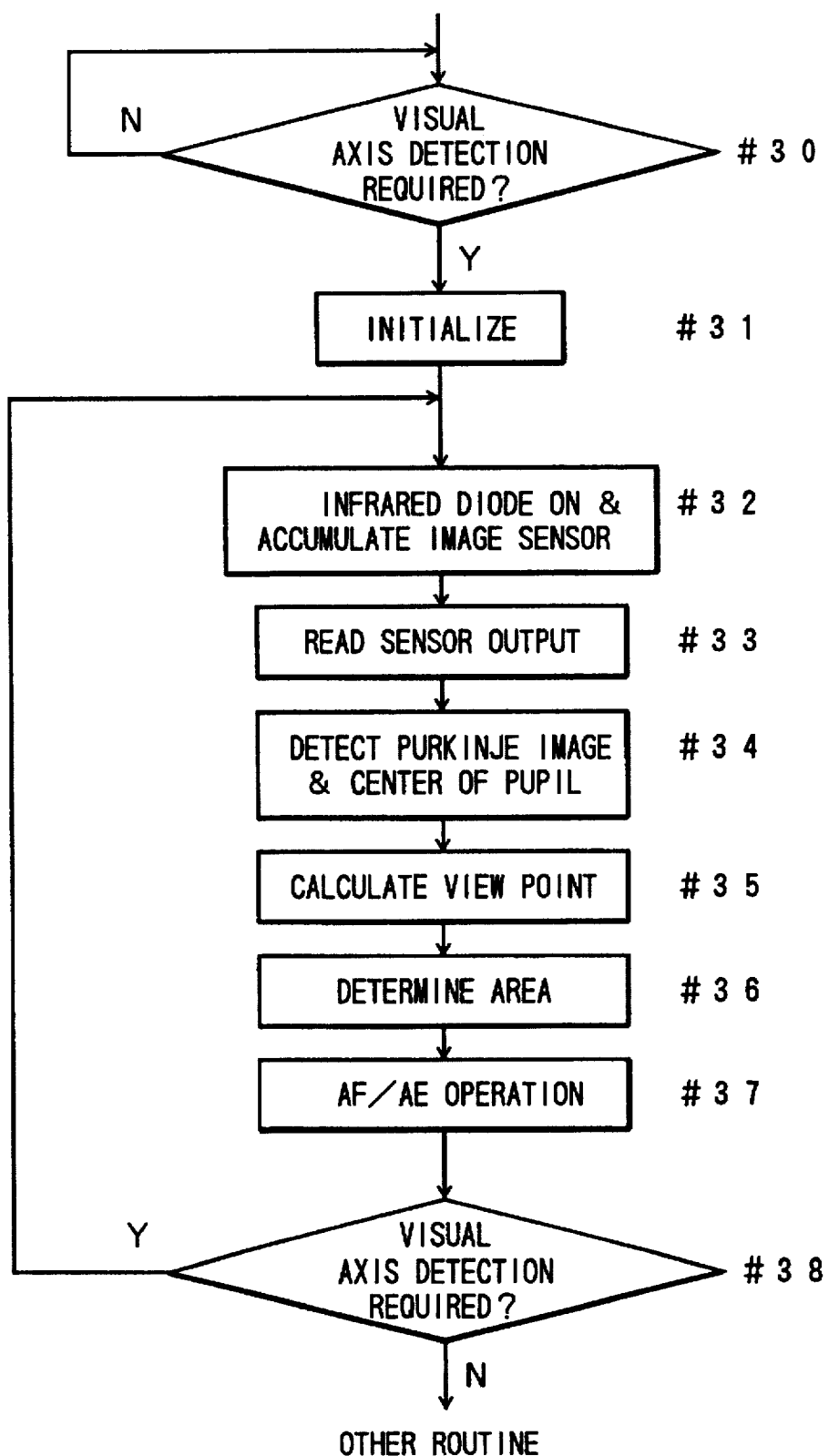
FIG. 6 is a flow chart of the second embodiment.

The operation procedure of the present embodiment is shown in FIG. 6.

When the visual axis detection demand switch (for example, the automatic pursuit switch) SW3 of the camera is closed to indicate the starting of visual axis detection, the M.P.U. 1 shifts its control to the visual axis detection routine.

When the visual axis detection routine is entered, the initializing process is first carried out to render all variables regarding visual axis detection into zero (step 31). Thereafter, the M.P.U. 1 gives an integrated signal and an illumination control signal synchronized therewith to the image sensor driving circuit 4 and the illumination control circuit 5, respectively, through the interface circuit 3. Thereby the infrared diode 7 is caused to emit light in synchronism with the accumulation in the image sensor 4 (step 32). Then, the image of the front eye part of the eyeball in which a Purkinje image formed on the image sensor 4 is created is read through the interface circuit 3 (step 33). By this image being processed, the rotation angles of the eyeball in the horizontal direction and the vertical direction are found, and further, by the correction of individual differences being effected, the photographer's view point on the image field is found (step 35). The area in which AF and AE are to be effected (which area is approximate to that of FIG. 3B) is determined on the basis of this view point (step 36), and AF, AE, etc. are effected on the basis of the information of this area (step 37). The operations of the steps 32–37 are repeated as long as the demand for visual axis detection continues (step 38). Again in this case, for the same reason as that set forth in the first embodiment, if the view point is outside the image field, it becomes necessary to bring the view point out of the object of the pursuing operation or to extract the photographer's view point by a conventional technique (e.g. the stay time) or the technique proposed in U.S. application Ser. No. 746,462 (filed on Aug. 16, 1991).

Figure 7:
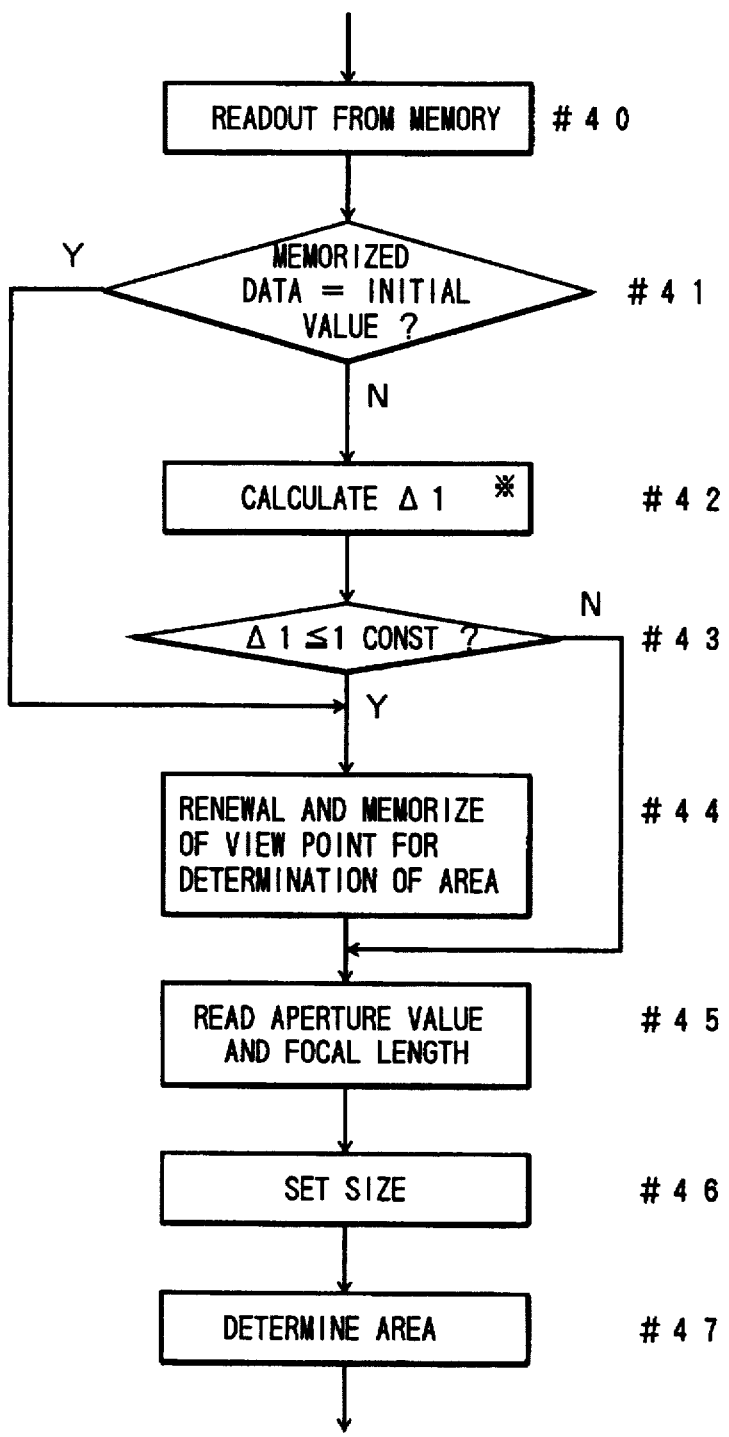
FIG. 7 is a flow chart of an operation for effecting the area determination of the second embodiment.
Figure 8:
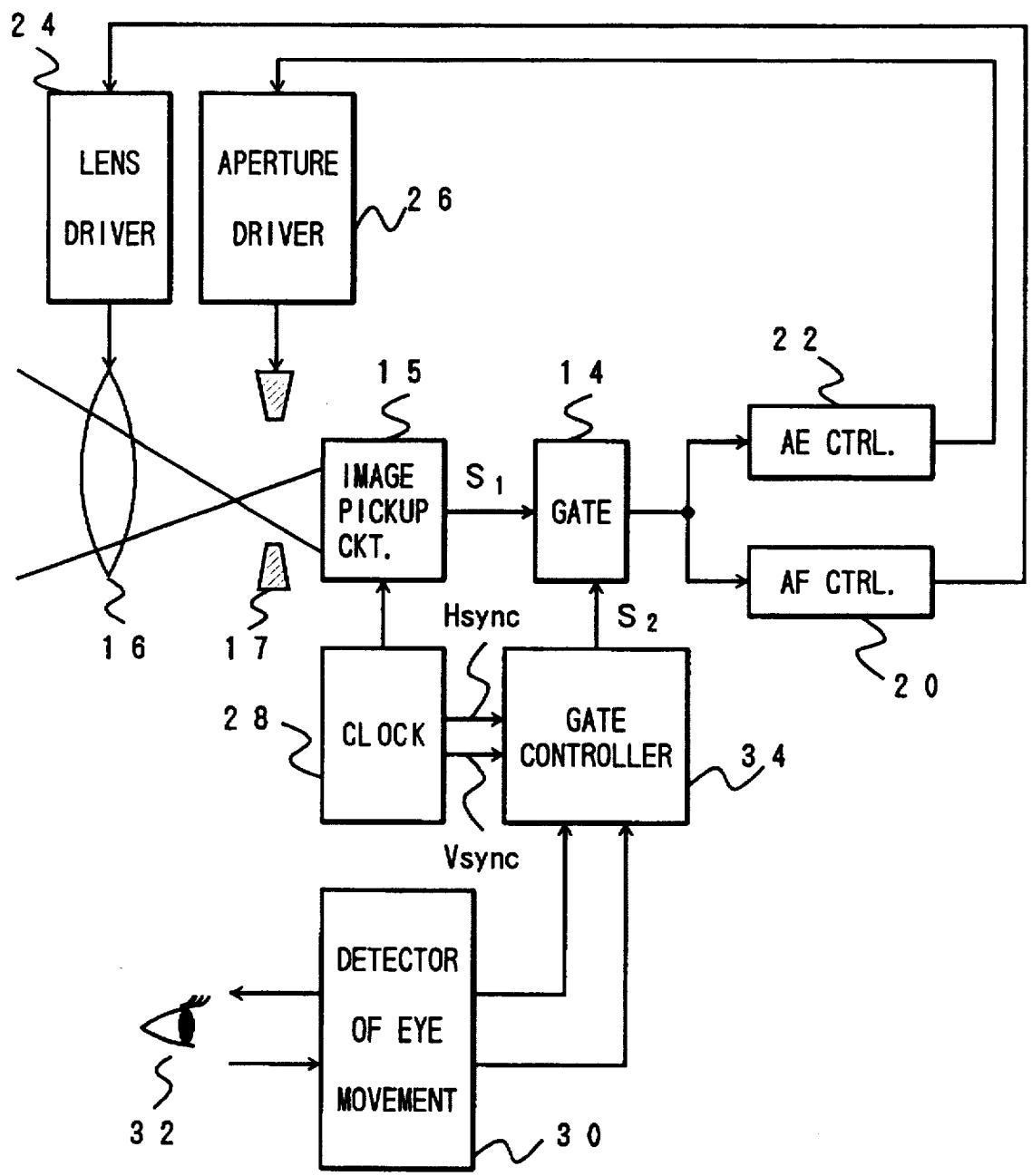
FIG. 8 shows the construction of an example of the prior art.
Figure 9:
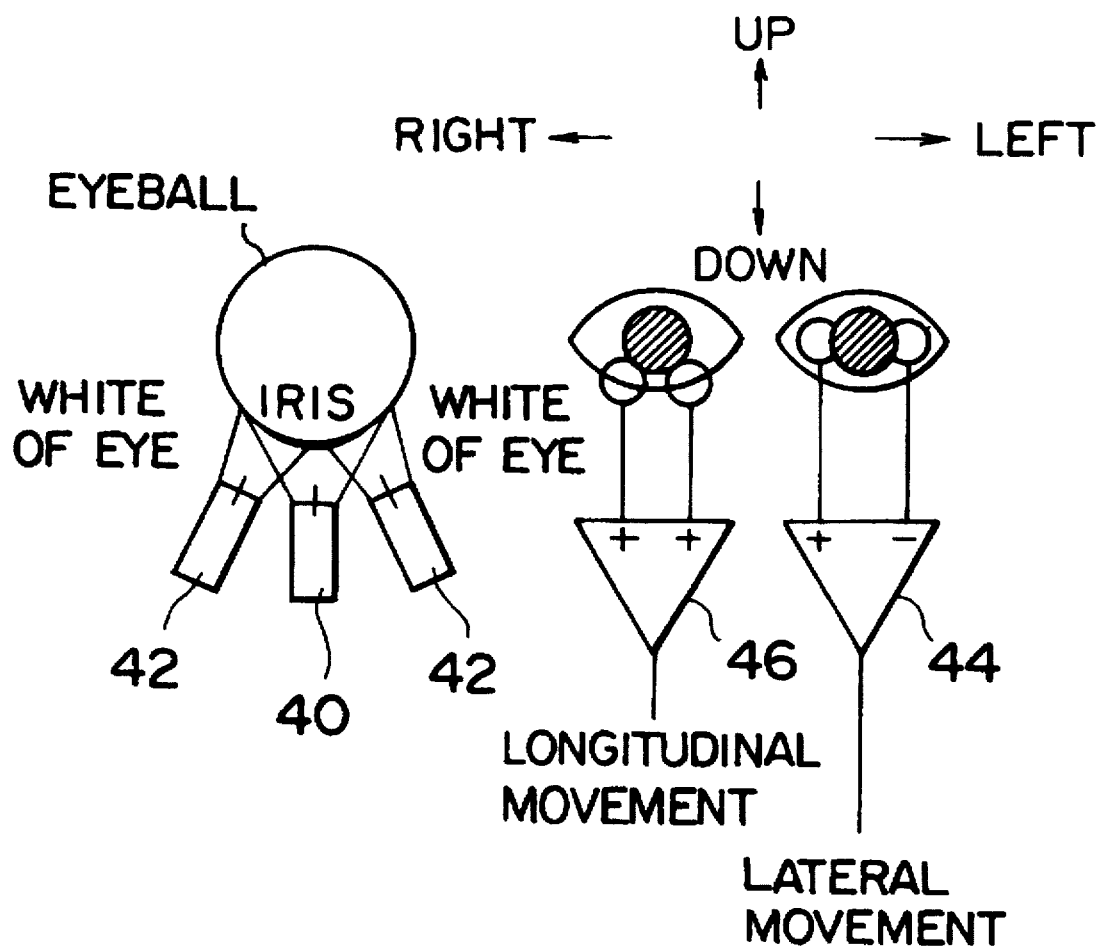
FIG. 9 illustrates the principle of the example of the prior art.
Figure 10:
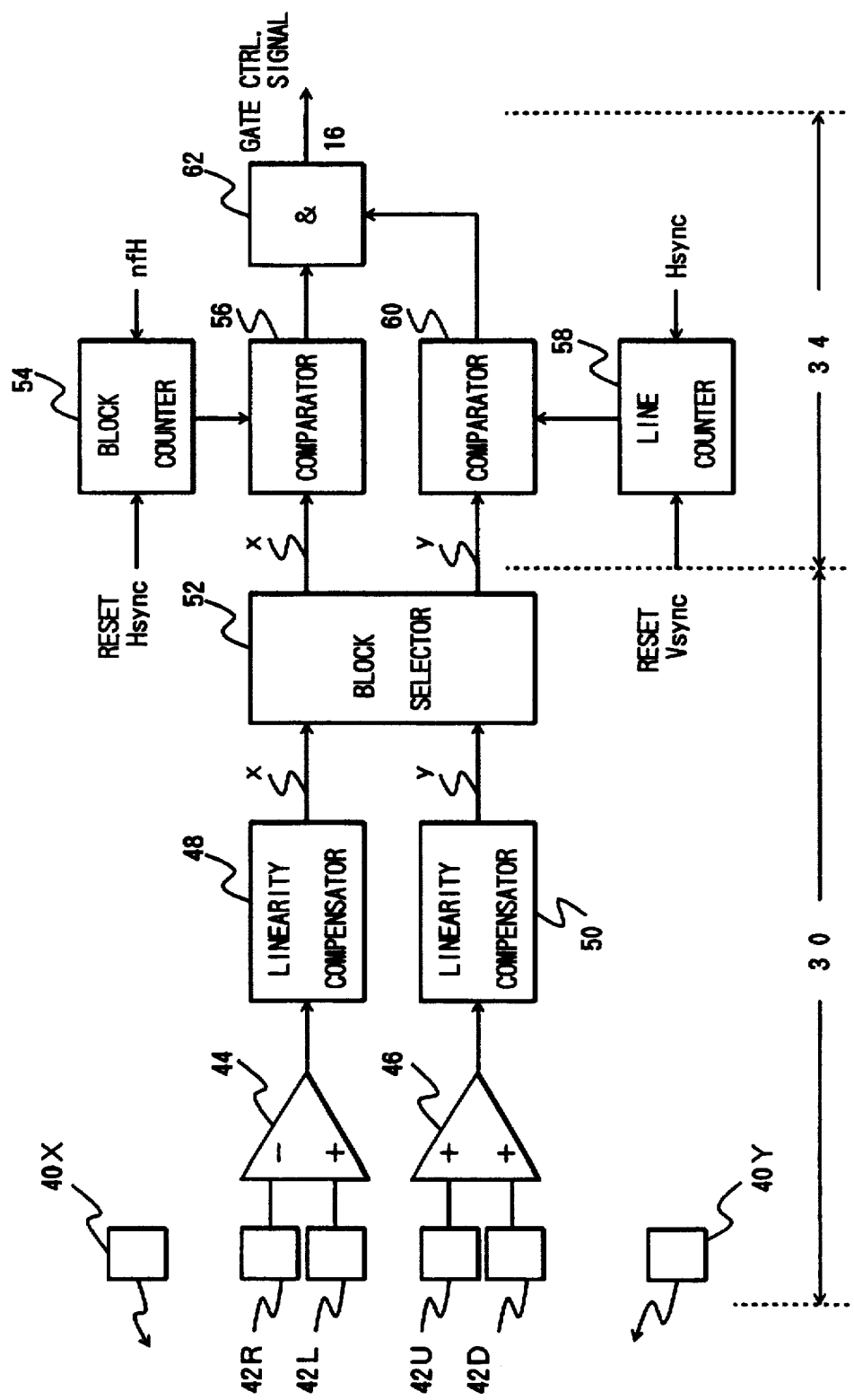
FIG. 10 is a circuit diagram of the example of the prior art.
Figures 11A, 11B:
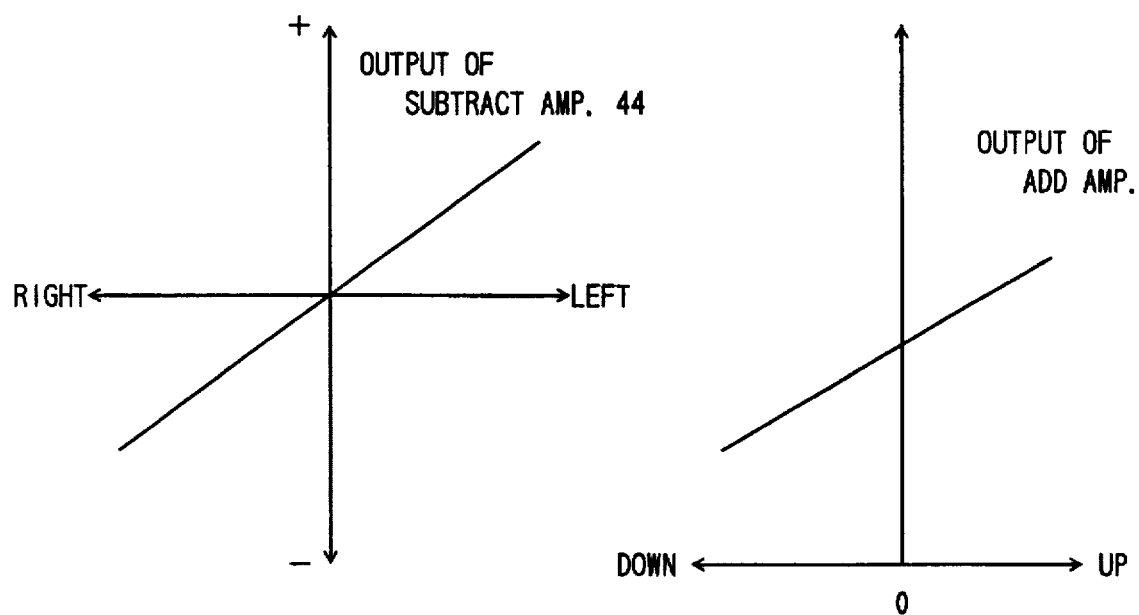
FIGS. 11A and 11B illustrate the example of the prior art.

Again in the present embodiment, in order to perform the pursuing operation effectively, the design is such that as in the first embodiment, the movement of the AF and AE area is not effected when the amount of movement of the view point exceeds a predetermined amount. The operation procedure for this is shown in FIG. 7. When the AF–AE area determination routine is entered from the view point position, the view point position information used for the last AF–AE area determination memorized in the memory is read (step 40). If it is an initialized value (step 41), the then view point position is memorized as a view point position $(x_0, y_0)$ for area determination into the memory, whereafter advance is made to the area setting routine (step 44). Also, in the case of the second or subsequent area determination, the aforementioned view point position is compared with the view point position for the last area determination. That is, the distance $\Delta 1=\sqrt{(x_i-x_{i-1})^2+(y_i-y_{i-1})^2}$ between the current view point position $(x_i, y_i)$ and the last view point position $(x_{i-1}, y_{i-1})$ is found (step 42), and if this value is equal to or less than a predetermined value 1const, the current view point position $(x_i, y_i)$ is memorized as the view point position $(x_0, y_0)$ for area determination into the memory, whereafter advance is made to the next routine. If conversely, $\Delta 1$ exceeds 1const, the view point position $(x_0, y_0)$ for area determination is not renewed, but advance is made to the next routine (step 43).

The determination of the AF and AE area is done in the following manner by the use of the view point position $(x_0, y_0)$ for area determination. The depth of field is first found from the then focal length and aperture value of the phototaking lens (step 45), and the size of the area is set in conformity with the value thereof (step 46). This is set so as to be small when the depth of field is shallow and to be large when the depth of field is deep. An area having a size conforming to the depth of field is determined about the view point position $(x_0, y_0)$ for area determination found at the preceding stage, and this is defined as the AF and AE area.

As long as the pursuing operation is performed, as described above, the AF and AE area is determined and moves in accordance with the movement of the object (the movement of the photographer's view point on the image field), and during the pursuing operation, the M.P.U. 1 outputs to the gate 14 the AF–AE area information determined in the manner described above. Thereby, the range of the image signal output from the gate 14 to the interface circuit 3 having the A/D converting function (the area in which AF and AE are effected) is set. The signal in the area of the image pickup element 15 output through the gate 14 is converted into a digital signal by the interface circuit 3, and thereafter is read into the M.P.U. 1. By the use of this signal, the M.P.U. 1 effects AF calculation and AE calculation to thereby calculate the amount of lens driving and the amount of aperture driving, and outputs the values thereof to the lens driving circuit 9 and the aperture driving circuit 11, respectively. In the two driving circuits, the lens and aperture are driven on the basis of those values. Then, the visual axis detection routine is again entered, and a new AF–AE area is set by the use of the calculated photographer's view point on the image field and the depth of field, and AF, AE, etc. are effected by the use of the signal from that area.

The above-described operations are repetitively performed, whereby the pursuing operation is accomplished.

In the video camcorder, AF calculation and AE calculation are effected by the use of an image signal output from the image pickup element and therefore, basically in any area of the entire image field, distance measurement and photometry are possible and the compensation for the AF point and the AE point as in a silver salt camera is unnecessary as a rule.

In the present invention, the design is made such that when the amount of movement of the photographer's visual axis exceeds a predetermined amount, the movement of the gaze position is not judged, whereby the inconvenience by the influence of saccadic movement or the like is eliminated.

Also, in the embodiments, provision is made of visual axis detecting means adopting "the detection principle using a Purkinje image and the center of the pupil" which can correctly detect the visual axis of the photographer looking into the finder in which the movement of the photographer's head and the rotational movement of the photographer's eyeball are mixedly present as in a camera, whereby it is made possible to discern the main object from the movement of the visual axis relative to a moving object and effect automatic pursuit.

Further, in the embodiments, pursuit (the movement of the AF–AE area) can be accomplished even in the following cases where pursuit cannot be accomplished well by an automatic pursuit system for changing the AF–AE area by image processing:

"A case where an object of the highest brightness exists in the background";

"A place which generally is dark";

"A case where a plurality of objects of the same brightness are irregularly moving";

"A case where the contrast of the object is low"; and

"A case where an object being pursued at a similar distance intersects another object (where the brightness of said another object is higher)".

A description will now be given of an embodiment which is further improved. In the above-described embodiments, when the distance when the view point determined by the result of detection shifts from the first point to the second point exceeds a predetermined distance, the detecting means detects a point in the course of the relatively fast saccadic movement of the eyeball as the view point or the photographer is judged to be seeing the outside of the photographing view field and the change of the view point to the second point is not primarily effected. In the following, a description will be given of an embodiment in which means for counting time is provided and if the photographer gazes at the second point at a predetermined distance for a predetermined time or longer, it is judged that the point is being gazed at and that point is dealt with as a new view point.

Figure 12:
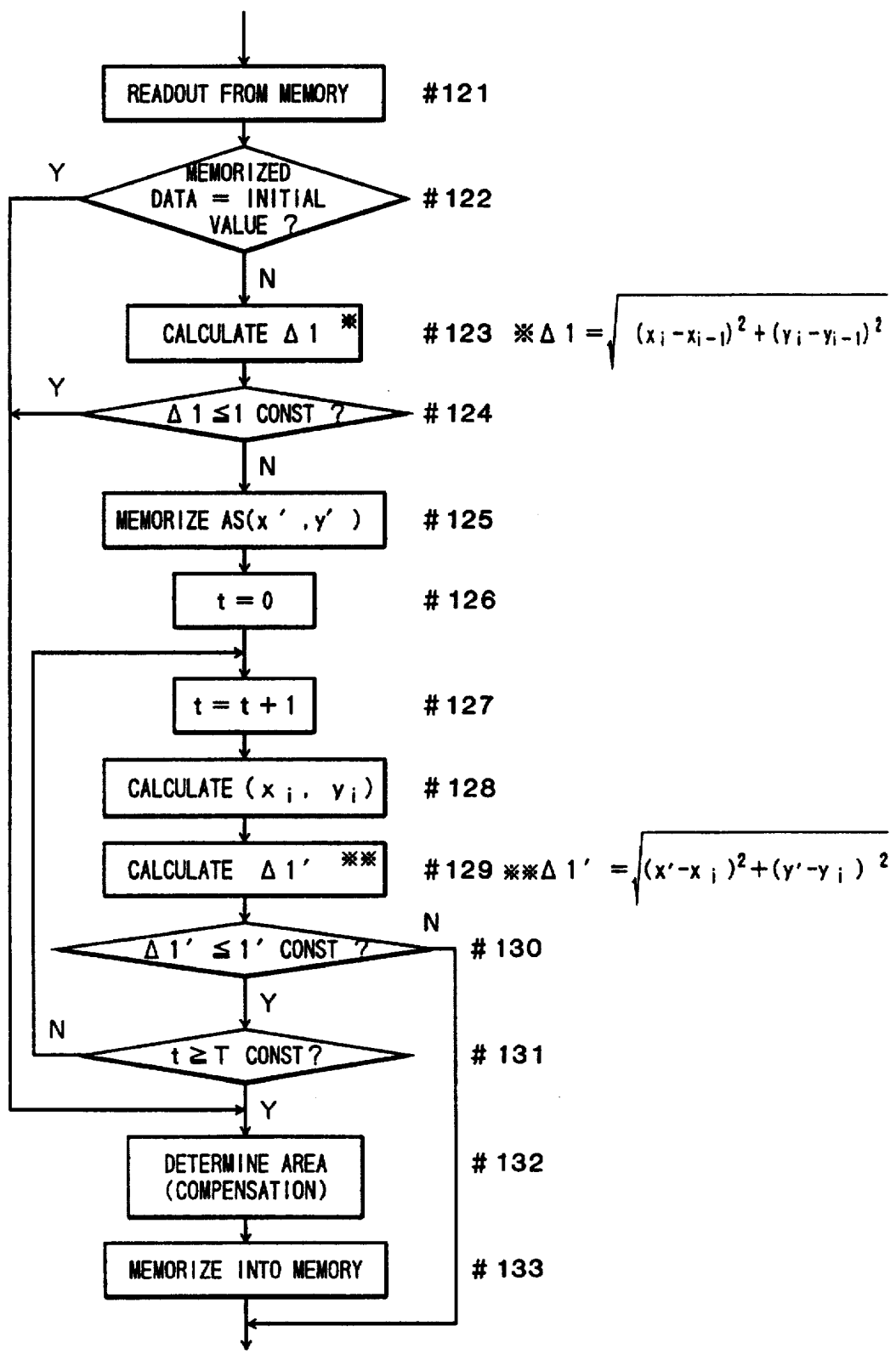
FIGS. 12 to 15 are flow charts of visual axis detection according to the present invention.

The operation procedure of the present embodiment is shown in FIG. 12, although there is some overlap with the previous description. When the AF–AE area determination routine is entered from the view point position, the information of the AF and AE area at the last view point position memorized in the memory is first read (step 121). If it is an initialized value, that is, if this operation is the first area determining operation (step 122), the compensation process as described above is carried out on the basis of the then view point position to thereby determine the area (step 132), and the information thereof is memorized into the memory (step 133). In the case of the second or subsequent operation, comparison with the information of the AF and AE area corresponting to the last view point position is effected (step 123), and whether there has been great movement is judged. If the x coordinates and y coordinates of the view point position used for the determination of the AF and AE area are memorized as the information of the AF and AE area, the distance $\Delta 1$ ($=\sqrt{(x_i-x_{i-1})^2+(y_i-y_{i-1})^2}$) between the view point position coordinates $(x_i, y_i)$ found this time and the last view point position coordinates $(x_{i-1}, y_{i-1})$ is found (step 123), and if this value is equal to or less than a predetermined value 1const (step 124), the view point position coordinates found this time is used and further, the above-described compensation process is carried out to thereby determine the area of a new view point position, and the information thereof is memorized into the memory. If conversely, $\Delta 1$ exceeds 1const, whether the visual axis stays at a position after movement for a predetermined time Tconst is judged. If it is judged that $\Delta 1 > 1$const (step 124), the view point position calculated this time is first memorized as (x', y') into the memory (step 125) and also, the value of the counter for counting time is rendered into zero (T=0) (step 126). Thereafter, the counter is counted up (step 127) and the photographer's view point at the next visual axis detection timing is calculated, and the coordinates of this position are defined as $(x_i, y_i)$ (step 128). The calculation of this view point, as previously described, is effected by turning on the infrared diode in synchronism with the accumulation in the image sensor, reading the image of the front eye part of the eyeball in which a Purkinje image is created, detecting the center of the Purkinje image pupil, and thereafter effecting calculations such as the correction of individual difference. Then, the difference $\Delta 1'(=\sqrt{(x'-x_i)^2+(y'-y_i)^2})$ between the position coodrinates $(x_i, y_i)$ of the thus calculated view point and the view point position coordinates (x', y') immediately after movement memorized in the memory is calculated (step 129), and if this value is greater than a constant 1'const determined with the minute movement of fixation taken into account, the change to the AF and AE area is not effected, but the process of this routine is terminated (step 130). If as a result, $t \geq$ Tconst, the visual axis is regarded as having stayed at the position after movement for a predetermined time Tconst or longer, and the position coordinates (x', y') of the view point found this time are used and further, the above-described compensation process is carried out to thereby determine the area (step 132), and the information thereof is memorized into the memory (step 133). If conversely, t<Tconst, the counter is counted up (step 127), whereafter a similar process is carried out, and if $\Delta 1' \leq 1'$const, the content of the counter is compared with Tconst. Thereafter, a similar process is carried out while the counter is counted up. That is, if after the visual axis has moved, the visual axis stays within a radius $\Delta 1'$ from that position (x', y') for the time Tconst or longer, this is regarded as an effective visual axis, and by the use of the position coordinates (x', y') of the view point after movement, the compensation process or the like is carried out to thereby effect the determination and change of the area.

As previously described, saccadic movement is eyeball movement occurring during reading or when one gazes at the feature of an image, and the movement time thereof is 1/20–1/100 second, and the maximum speed thereof amounts to 300 degrees/sec. But the occurrence period thereof does not become a short interval less than 0.2 second, and further in the movement state from 50 msec. before the occurrence of the movement till the termination of the movement, there is seen the phenomenon that visual function called saccadic suppression is extremely reduced.

Accordingly, with regard to an erroneous operation caused by detecting a point in the course of movement to the movement termination point when saccadic movement has occurred, particularly to saccadic movement which has occurred to see the display outside the finder view field, it is expected that a great inconvenience will occur if the point in the course of movement is detected. Consequently, the constant 1const is determined by pursuing movement (which is slow and smooth eyeball movement occurring when one pursues a moving object slowly, and occurs for a moving object of 30–35 degrees/sec. or less) and visual axis detection interval. Thus, the constant 1const is determined in the form of the product of the amount of movement 1smooth of the view point on the focusing screen of the camera caused by the pursuing movement and the visual axis detection interval Tsample. Also, 1'const is set so as to cover the movement range of the minute movement of fixation (which is irregular minute movement involuntarily occurring to grasp the image of an object at the central eddy of the eyeball and hold that state, and has the role of always fluctuating the stimulus of light to the visual cell of the central eddy and not reducing the signal 1 production efficiency). Tconst is determined by the period of occurrence of saccadic movement.

Turning back to FIG. 2, when the photometry switch SW1 is closed (step 17), the AF operation and photometry are effected (steps 18 and 19). In the AF operation, the M.P.U. 1 first reads the signal of a portion corresponding to the AF area on the gaze line determined from the sensor and calculates that signal to thereby find the amount of lens driving. Thereafter, the M.P.U. 1 controls the lens driving unit and effects focus adjustment. Also, the M.P.U. 1 finds exposure constants (shutter speed, aperture value, etc.) in accordance with a designated photographing mode on the basis of a signal from the photometry sensor.

When release is required, a series of operations concerned with release such as the driving of the aperture to the calculated aperture value, the opening and closing of the shutter, the mirror operation and the winding of film are performed.

In the description hitherto made, the AF operation (signal reading→calculation→lens driving) and photometry have been described as being effected substantially at a time, but in the actual camera, the AF operation and photometry conform to a mode set in the camera. That is, upon setting of the mode of the camera, photometry may be effected immediately before release and the exposure value may be determined on the basis of the photometric value.

Figure 13:
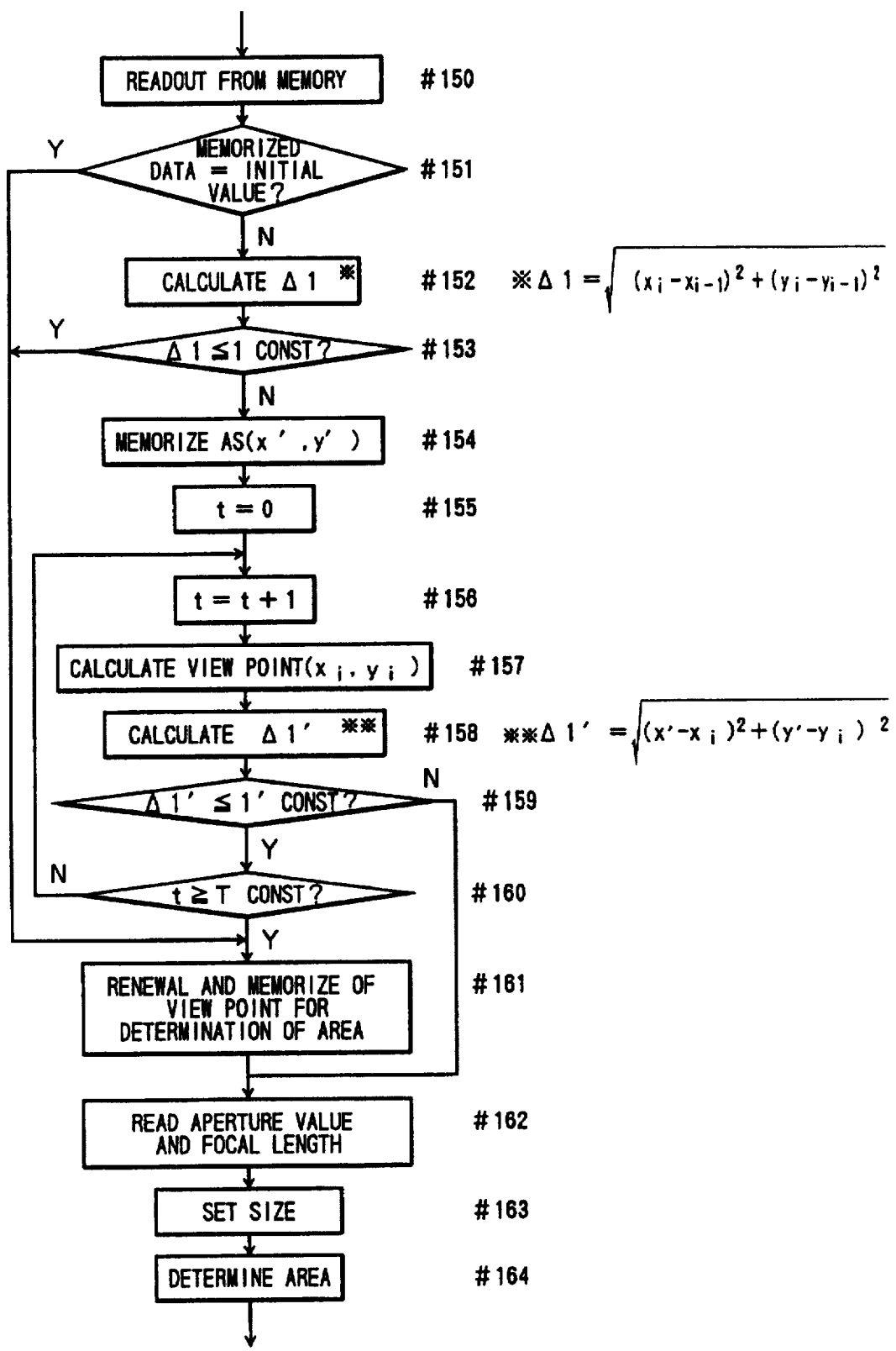

A description will now be given of an embodiment when the view point detecting apparatus of the present invention is applied to the video camera shown in FIGS. 5 and 6. The operation procedure of this embodiment is shown in FIG. 13. When the AF–AE area determination routine is entered from the view point position, the information of the last AF and AE area memorized in the memory is first read (step 150). If it is an initialized value (step 151), the then view point position is memorized as a view point position $(x_0, y_0)$ for area determination into the memory (step 161), whereafter advance is made to the area setting routine. In the case of the second or subsequent operation, comparison is made with the last view point position for area determination. That is, the distance $\Delta 1$ ($=\sqrt{(x_i-x_{i-1})^2+(y_i-y_{i-1})^2}$) between the current view point position $(x_i, y_i)$ and the last view point position $(x_{i-1}, y_{i-1})$ is found (step 152), and if this value is equal to or less than a predetermined value 1const (step 153), the current view point position $(x_i, y_i)$ is memorized as the view point position $(x_0, y_0)$ for area determination into the memory (step 161), whereafter advance is made to the area setting routine. If conversely, $\Delta 1$ exceeds 1const, whether the visual axis stays at the position after movement for a predetermined time Tconst is judged. The view point position after movement is first memorized as $(x', y')$ (step 154), and then the counter is reset (steps 155 and 156) and time counting is started. If the amount of movement $\Delta 1'$ (= $\sqrt{(x'-x_i)^2+(y'-y_i)^2}$) (step 158) of a newly calculated view point position $(x_i, y_i)$ (step 157) from $(x_i, y_i)$ is equal to or less than a constant 1'const determined from the characteristic of the minute movement of fixation (step 159), the counter is counted up (step 156). If the value t of the counter becomes equal to or greater than Tconst or (step 160) , $(x', y')$ is memorized as a view point position $(x_0, y_0)$ for area determination into the memory (step 161), whereafter advance is made to the area setting routine. If conversely, movement exceeding 1'const occurs before the value t of the counter reaches Tconst, the view point position $(x_0, y_0)$ for area determination is not renewed, but advance is made to the next routine.

The determination of the AF and AE area is accomplished in the following manner by the use of the view point position $(x_0, y_0)$ for area determination. The depth of field is first found from the then focal length and aperture value of the photo-taking lens, and the size of the area is determined in conformity with the value thereof. This is set so as to be small when the depth of field is shallow and to be large when the depth of field is deep. Then, an area having a size conforming to the depth of field is determined about the view point position $(x_0, y_0)$ for area determination found at the preceding stage (step 163), and this is defined as the AF and AE area (step 164).

As long as the pursuing operation is performed, as described above, the AF and AE area is determined and moves in accordance with the movement of the object (the movement of the photographer's view point on the image field). During the pursuing operation, the M.P.U. 1 outputs to the gate 14 the AF and AE area information corresponding to the view point position determined in the manner described above. Thereby, the range of the image signal output from the gate 14 to the interface circuit 3 having the A/D converting function (the area in which AF and AE are effected) is set.

The signal in the area of the image pickup element 15 output through the gate is converted into a digital signal by the interface circuit 3, and thereafter is read into the M.P.U. 1. By the use of this signal, the M.P.U. 1 effects AF calculation and AE calculation and calculates the amount of lens driving and the amount of aperture driving, and outputs the values thereof to the lens driving circuit 9 and the aperture driving circuit 11, respectively. In the two driving circuits, the lens and aperture are driven on the basis of those values. Then, the visual axis detection routine is again entered, and by the use of the calculated photographer's view point on the image field and the depth of field, a new AF and AE area is set, and AF and AE operations are performed by the use of a signal from that area.

By the above-described operations being repetitively performed, the pursuing operation is accomplished.

In the video camcorder, AF calculation and AE calculation are effected by the use of an image signal output from the image pickup element and therefore, basically in any area of the entire image field, distance measurement and photometry are possible, and the compensation process for the AF point and the AE point as in a silver salt camera is unnecessary as a rule.

The above embodiments have been described with respect chiefly to an apparatus in which the detection error caused by the saccadic movement of the eyeball is mitigated. In the following, a description will be given of an embodiment in which the detection error caused by the minute movement of fixation of the eyeball is mitigated. The minute movement of fixation, which will be described later in detail, refers to movement in which even in a gazing state, the gaze point strictly is always moving vehemently. An embodiment in which the measuring area is prevented from fluctuating during each such minute movement will be described below.

Figure 14:
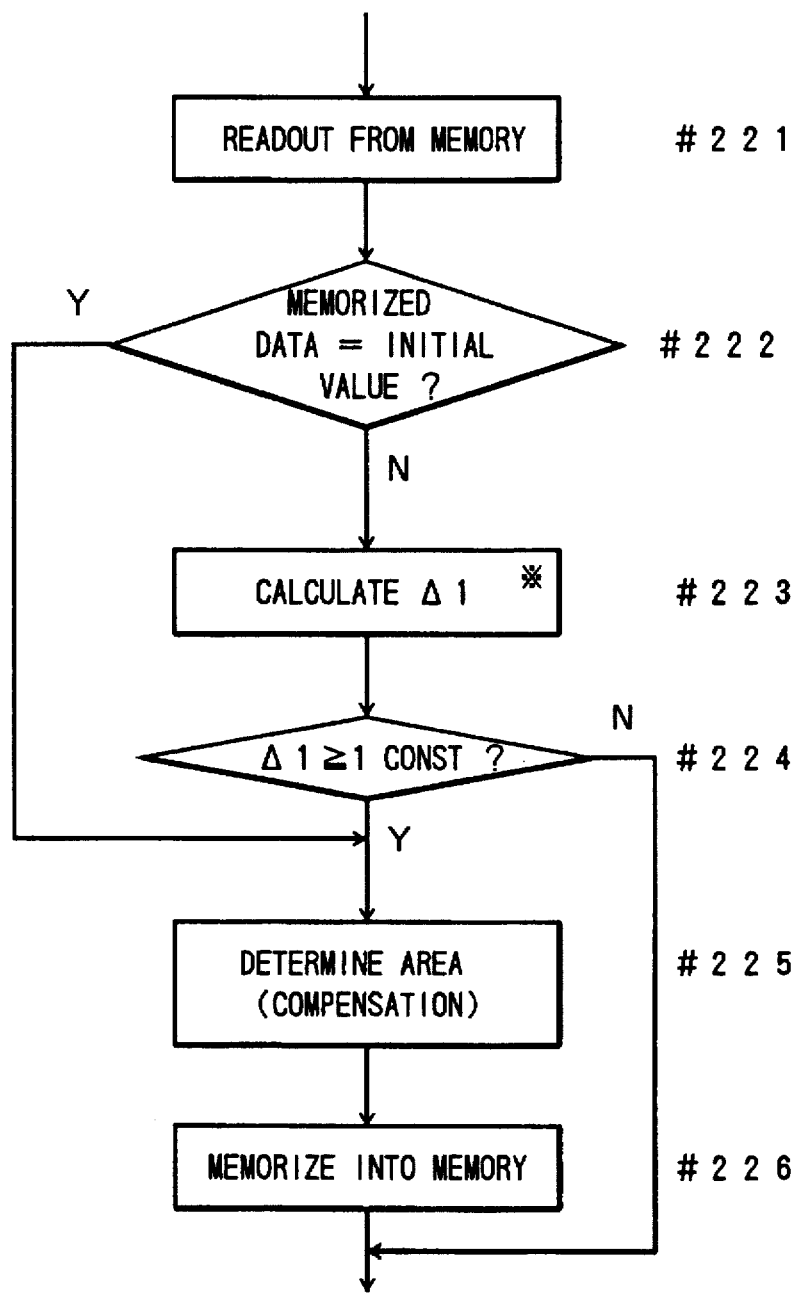

In this embodiment, the design is such that in order to perform the pursuing operation effectively, the movement of the AF and AE area is not effected when the amount of movement of the view point is less than a predetermined value. The operation procedure for that is shown in FIG. 14. When the AF–AE area determination routine is entered from the gaze position, the information of the AF and AE area at the last gaze position memorized in the memory is first read (step 221). If it is an initialized value, that is, if the operation is the first area determining operation (step 222), the compensation process as described above is carried out on the basis of the then position of the view point to thereby determine the area (step 225), and the information thereof is memorized into the memory (step 226). In the case of the second or subsequent operation, comparison is made with the information of the last AF and AE area, and whether there is a sufficient distance between the current and last AF and AE areas is judged. Where as the information of the AF and AE area, the coordinates of the view point used during the determination thereof are memorized, the distance $\Delta 1$ (= $\sqrt{(x_i-x_{i-1})^2+(y_i-y_{i-1})^2}$) between the coordinates $(x_i, y_i)$ of the view point found this time and the coordinates $(x_{i-1}, y_{i-1})$ of the last view point position is found (step 223), and if this value is equal to or greater than a predetermined value 1const (step 224), the coordinates $(x_i, y_i)$ of the view point found this time is used to further carry out the above-described compensation process to thereby determine the area of a new gaze position, and the information thereof is memorized into the memory. If conversely, $\Delta 1$ is less than 1const, the area information found the last time is not renewed but is used intact.

The purpose of carrying out such a process is to minimize a detection error attributable to the characteristic of man's eyeball movement and suppress an erroneous operation or an inconvenience caused by changing over the AF and AE area cumbersomely (for example, the inconvenience that just when the view point moves slightly between two AF areas, the lens is reciprocally moved between the two when one of the two AF areas is a main object and the other is the background).

The characteristic of the eyeball movement taken up here as a subject is the minute movement of fixation. The minute movement of fixation is irregular minute movement involuntarily occurring to grasp the image of an object in the central eddy of the eyeball and hold that state. This minute movement has the role of always fluctuating the stimulus of light to the visual cell of the central eddy and not reducing the signal production efficiency.

Accordingly, this minute movement of fixation occurs when the photographer gazes at a certain object. The constant 1const is set so as to cover the range of the minute movement of fixation (usually 0.5 mm or less on the focusing screen) so that the AF and AE area may not be varied by the minute movement of fixation which has occurred.

Figure 2:
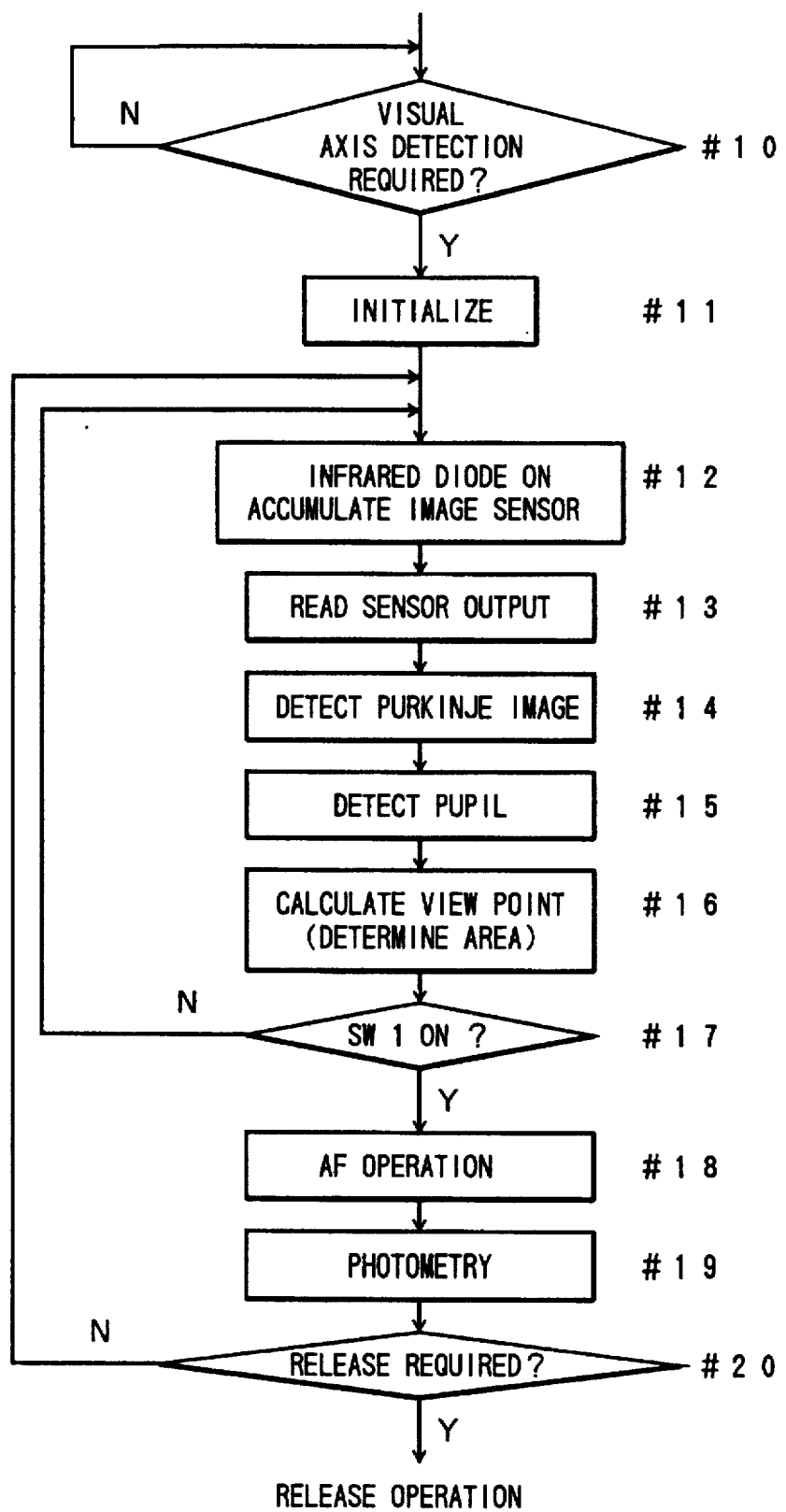
FIG. 2 is a flow chart of the first embodiment.

Return is then made to the routine of the step 17 shown in FIG. 2. The description of it is omitted herein.

Figure 15:
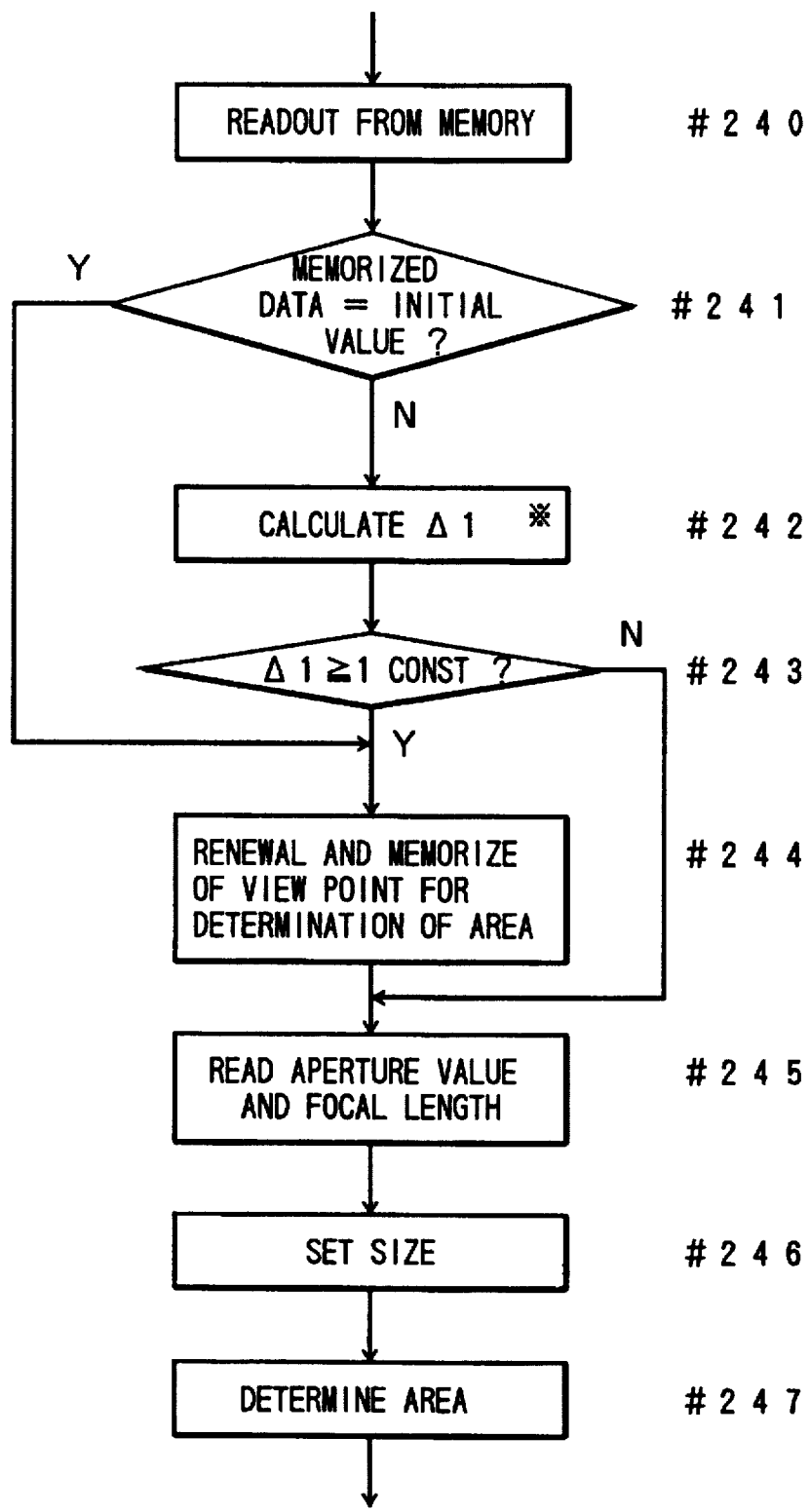

The previous embodiment is a system suitable for a silver salt still camera, whereas the next embodiment shown in FIG. 15 is a system suitable for a video camcorder or the like, as shown in FIG. 5. Also, the principle of visual axis detection, like that of the previous embodiment, uses a Purkinje image and the center of the pupil.

The basic operation procedure of the present embodiment is the same as that shown in FIG. 6.

Again in the present embodiment, in order to perform the pursuing operation effectively, the design is such that as in the previous embodiment, the movement of the AF and AE area is not effected when the amount of movement of the view point is less than a predetermined value. The operation procedure of it is shown in FIG. 15. When the AF and AE area determination routine is entered from the view point position, the view point position information used in the last AF and AE area determination which is memorized in the memory is read (step 240). If it is an initialized value (step 241), the then view point position is memorized as a view point position $(x_0, y_0)$ for area determination into the memory, whereafter advance is made to the area setting routine (step 244). Also, in the case of the second or subsequent operation, comparison is made with the last view point position for area determination and if there is a sufficient distance therebetween, the distance $\Delta l$ (= $\sqrt{(x_i-x_{i-1})^2+(y_i-y_{i-1})^2}$) between the current view point position $(x_i, y_i)$ and the last view point position $(x_{i-1}, y_{i-1})$ is found (step 242), and if this value is equal to or greater than a predetermined value lconst, the current view point position $(x_i, y_i)$ is memorized as a view point position $(x_0, y_0)$ for area determination into the memory, whereafter advance is made to the next routine (step 243).

The determination of the AF and AE area is accomplished in the following manner by the use of the view point position $(x_0, y_0)$ for area determination. The depth of field is found from the then focal length and aperture value of the photo-taking lens (step 245), and in conformity with the value thereof, the size of the area is determined (step 246). This is set so as to be small when the depth of field is shallow, and to be large when the depth of field is deep. Then, an area having a size conforming to the depth of field is determined about the view point position $(x_0, y_0)$ for area determination found at the preceding stage, and this is defined as the AF and AE area (step 247).

As long as the pursuing operation is performed, as described above, the AF and AE area is determined and moves in accordance with the movement of the object (the movement of the photographer's view point on the image field). During the pursuing operation, the M.P.U. 1 outputs to the gate 14 the AF and AE area information determined in the manner described above. Thereby the range of the image signal output from the gate 14 to the interface circuit 3 having the A/D converting function (the area in which AF and AE are effected) is set.

In the above-described embodiment, the design is such that in the case of a small amount of movement of the visual axis like the minute movement of fixation, the change of the area is not effected, but a similar effect can be obtained even if the change of the area is not effected when the photographer's eye is turned to the outside of the finder. In that case, it can be accomplished by adding the step of "$\Delta l \leq l\max$" after the step 223 of FIG. 14 and the step 243 of FIG. 15, and setting "$l\max$" here to a great value.

In the present invention, the design is such that when the amount of movement of the photographer's visual axis (view point) is less than a predetermined value, the movement of the gaze position is not judged, thereby eliminating the inconvenience such as the influence of the minute movement of fixation or the like.

Also, in the embodiments, the area for obtaining the information when AF, AE, etc. are effected is determined on the basis of the output of the visual axis detecting function (the photographer's view point on the image field), and this area is moved in conformity with the output from the visual axis detecting means, whereby the pursuing operation of higher accuracy which has overcome the disadvantages peculiar to the prior art is made possible.

What is claimed is:

1. A view point detecting apparatus comprising:

first detecting means for detecting a view point information; and second detecting means for detecting an amount of variation in a first view point information and a subsequent second view point information detected by said first detecting means and for determining said first view point information as an effective view point information when said amount of variation exceeds a standard value.

2. A view point detecting apparatus according to claim 1, further comprising means for effecting focus adjustment of a photo-taking lens on the basis of said first view point information.

3. A view point detecting apparatus according to claim 1, wherein said standard value consists of a value related to a saccadic eye movement.

4. A view point detecting apparatus according to claim 1, wherein each of said first view point information and said second view point information comprises respective position information.

5. A view point detecting apparatus comprising:

detecting means for detecting a view point information; and changing means for changing information from a first view point information to a subsequent second view point information, after detection of said first and second view point information by said detecting means, when an amount of variation from said second view point information to said first view point information exceeds a first standard value and an amount of variation from said second view point information to a third view point information detected by said detecting means does not exceed a second standard value for a time longer than or equal to a predetermined time.

6. A view point detecting apparatus according to claim 5, further comprising means for effecting focus adjustment of a photo-taking lens on the basis of said second view point information.

7. A view point detecting apparatus according to claim 3, wherein said second standard value consists of a value related to a minute eye movement of fixation.

8. A view point detecting apparatus according to claim 5, wherein each of said first view point information and said second view point information comprises respective position information.

9. A view point detecting apparatus comprising:

first detecting means for detecting a view point position; and second detecting means for detecting a difference between a first view point position and a subsequent second view point position detected by said first detecting means and for determining said first view point position as an effective view point position when said difference is below a standard value, and for determining said second view point position as an effective view point position when said difference is greater than or equal to said standard value.

10. A view point detecting apparatus according to claim 9, further comprising means for effecting focus adjustment of a photo-taking lens on the basis of said first view point information.

11. A view point detecting apparatus according to claim 9, wherein said standard value consists of a value related to a minute eye movement of fixation.

12. A view point detecting apparatus according to claim 9, wherein each of said first view point information and said second view point information comprises respective position information.

13. An image taking apparatus comprising:

first detecting means for detecting a state of a view point; and second detecting means for detecting an amount of variation in a first view point information and a subsequent second view point information detected by said first detecting means and for determining said first view point information as an effective view point information when said amount of variation exceeds a standard value.

14. An image taking apparatus according to claim 13, further comprising means for effecting focus adjustment of a photo-taking lens on the basis of said first view point information.

15. An image taking apparatus according to claim 13, wherein said standard value consists of a value related to a saccadic eye movement.

16. An image taking apparatus according to claim 13, wherein each of said first view point information and said second view point information comprises respective position information.

17. An image taking apparatus comprising:

detecting means for detecting a state of a view point; and changing means for changing information from a first view point information to a subsequent second view point information, after detection of said first and second view point information by said detecting means, when an amount of variation from said second view point information to said first view point information exceeds a first standard value and an amount of variation from said second view point information to a third view point information detected by said detecting means does not exceed a second standard value for a time longer than or equal to a predetermined time.

18. An image taking apparatus according to claim 17, further comprising means for effecting focus adjustment of a photo-taking lens on the basis of said second view point information.

19. An image taking apparatus according to claim 17, wherein said second standard value consists of a value related to a minute eye movement of fixation.

20. An image taking apparatus according to claim 17, wherein each of said first view point information and said second view point information comprises respective position information.

21. An image taking apparatus comprising:

first detecting means for detecting a view point position; and second detecting means for detecting a difference between a first view point position and a subsequent second view point position detected by said first detecting means and for determining said first view point position as an effective view point position when said difference is below a standard value, and for determining said second view point position as an effective view point position when said difference is greater than or equal to said standard value.

22. An image taking apparatus according to claim 21, further comprising means for effecting focus adjustment of a photo-taking lens on the basis of said first view point information.

23. An image taking apparatus according to claim 21, wherein said standard value consists of a value related to a minute eye movement of fixation.

* * * * *

UNITED STATES PATENT AND TRADEMARK OFFICE
CERTIFICATE OF CORRECTION

PATENT NO.   : 5,546,158
DATED        : August 13, 1996
INVENTOR(S)  : KAZUKI KONISHI, ET AL.

It is certified that error appears in the above-indentified patent and that said Letters Patent is hereby corrected as shown below:

Column 2,
    line 25, "applications" should read --Applications--; and
    line 27, "applications" should read --Applications--.
Column 5,
    line 33, "and" should read --and to--.
Column 7,
    line 11, "application" should read --Application--.
Column 9,
    line 16, "is" should read --are--.
Column 11,
    line 16, "or" (second occrrence) should be deleted.
Column 13,
    line 65, "-1max" should read --1max--.
Column 14,
    line 54, "3," should read --5,--.

Signed and Sealed this

Eleventh Day of February, 1997

BRUCE LEHMAN

Attest:

Attesting Officer

Commissioner of Patents and Trademarks